(12) United States Patent
Van Hal et al.

(10) Patent No.: US 7,764,380 B2
(45) Date of Patent: Jul. 27, 2010

(54) HAIR DETECTION DEVICE

(75) Inventors: Robbert Adrianus Maria Van Hal, Eindhoven (NL); Rieko Verhagen, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 776 days.

(21) Appl. No.: 11/578,734

(22) PCT Filed: Apr. 15, 2005

(86) PCT No.: PCT/IB2005/051240

§ 371 (c)(1),
(2), (4) Date: Oct. 17, 2006

(87) PCT Pub. No.: WO2005/102153

PCT Pub. Date: Nov. 3, 2005

(65) Prior Publication Data

US 2007/0252997 A1    Nov. 1, 2007

(30) Foreign Application Priority Data

Apr. 20, 2004   (EP) ................... 04101619

(51) Int. Cl.
*G01N 21/55* (2006.01)
(52) U.S. Cl. ...................................... 356/445
(58) Field of Classification Search ................. 356/445; 606/9; 607/88
See application file for complete search history.

(56) References Cited

U.S. PATENT DOCUMENTS

| | | | |
|---|---|---|---|
| 6,955,672 B2 * | 10/2005 | Cense et al. ................... 606/9 |
| 6,976,984 B2 * | 12/2005 | Cense et al. ................... 606/9 |
| 2003/0036751 A1 * | 2/2003 | Anderson et al. ............... 606/9 |
| 2003/0050561 A1 | 3/2003 | Bazin et al. |
| 2008/0255548 A1 * | 10/2008 | Van Hal et al. ............... 606/10 |

FOREIGN PATENT DOCUMENTS

| WO | WO 9911324 A1 * | 3/1999 |
| WO | WO 00 62700 | 10/2000 |
| WO | WO 2004 008114 | 1/2004 |

* cited by examiner

*Primary Examiner*—Roy Punnoose

(57) ABSTRACT

A hair-detection device with a source of electromagnetic radiation, an imaging sensor and a radiation selection means. The selection means improves a ratio between a part of emitted radiation that is coupled into a skin which reaches the sensor and thus provides an image of the skin, and the part that reaches the sensor via other ways, such as reflection at the skin surface. The radiation may have a wavelength between about 700 nm and 1100 nm. The radiation selection means may for example include a separate wall around at least one of the source and the sensor, such as crossed polarizers. By means of this selection, the contrast of the image may be improved, and may be made less dependent on skin color and skin artifacts, thus enabling easier detection of for example, white hairs on a fair skin.

18 Claims, 3 Drawing Sheets

HAIR DETECTION DEVICE

BACKGROUND OF THE INVENTION

The present invention relates to a hair-detection device, comprising a source of electromagnetic radiation and an imaging sensor for determining an image of a part of a skin to be illuminated by said radiation, which imaging sensor is sensitive to at least a predetermined wavelength range of said electromagnetic radiation.

From WO 00/62700 there is known a hair-detection device of the kind mentioned in the opening paragraph, which is used in a hair-removing device, the hair-detection device comprising an illumination member for illuminating a skin portion, an image sensor and a control unit for processing the image in order to detect on the skin portion a position and/or orientation of a hair.

A disadvantage of the known hair-detection device is that it is very difficult to detect hairs under certain circumstances, in particular low-contrast circumstances, such as white or fair hair on a fair skin or heavily pigmented hair on a dark skin.

SUMMARY OF THE INVENTION

It is an object of the present invention to provide a hair-detection device of the kind mentioned in the opening paragraph, that offers improved hair detection, especially under low-contrast circumstances.

According to the present invention, said object is achieved with a hair-detection device of the kind mentioned in the opening paragraph, that is characterized in that said predetermined wavelength range is comprised in the range from 700 nm to 2000 nm, and that the hair-detection device further comprises radiation selection means for increasing the ratio of the intensity of radiation within said wavelength range that is receiveable by said imaging sensor after having traveled through said skin, to the intensity of radiation within said wavelength range that is receiveable by said imaging sensor without having traveled through said skin.

The inventors have realized that radiation that is actually coupled into the skin and is scattered within the skin before leaving the skin may be better suited for this purpose than other parts of the radiation, for example specularly reflected radiation. The wavelength range of about 700 nm to about 2000 nm comprises radiation that is easily coupled into the skin, is only poorly absorbed by the skin tissue, and will be sufficiently scattered to produce a quasi-homogeneous illumination of the skin portion to be imaged. Said quasi-homogeneous illumination causes hairs that are present on the skin portion to create a shadow that is clearly recognizable in the image as being a hair. This shadow formation mainly depends on the geometry of the hair and differences in the refractive index of the hair and its surroundings, i.e. air or skin tissue. The imaging is less dependent on the pigment color and the absorption caused thereby. Hence the imaging is generally hair color-independent. Absorption of radiation or unwanted contrasts due to skin pigments, freckles, port-wine stains etc. is also low in this wavelength region.

Moreover, artifacts or other imaging disturbing features, such as those introduced by specular reflection of radiation at the skin, are suppressed by improving the ratio between radiation that is made quasi-homogeneous before leaving the skin and radiation that would reach the imaging sensor either directly, via (specular) reflection at the skin or via any other path that does not lead the radiation through the skin.

In principle, from a quantum mechanical point of view, even reflected or scattered radiation enters the skin, albeit over only a very short distance. Furthermore, even short wavelength radiation may enter the skin and be scattered and re-emitted. However, this will relate to only a very small part of the radiation, exceedingly small for larger penetration depths and shorter wavelengths. Therefore, preferably, the radiation selection means increase the ratio of the intensity of radiation within said wavelength range that is receiveable by said imaging sensor after having traveled through said skin below the epidermis layer thereof, and the intensity of radiation within said wavelength range that is receiveable by said imaging sensor without having traveled through said skin below the epidermis layer thereof. The epidermis layer may be regarded as indicative of the penetration depth that discerns desired radiation from undesired radiation. Although the thickness of the epidermis layer varies over the body, and from person to person, it may be said that the radiation that is able to penetrate through the epidermis layer and back again, will also be useful in the present device. Since the epidermis contains much of the pigmentation of the skin, radiation having a shorter wavelength than about the above-mentioned 700 nm will be absorbed for a large part. For practical purposes, scattering to a homogeneous radiation may be insufficient before a substantial amount of that radiation is absorbed, especially in view of discomfort or even pain or injury experienced by the treated subject. For wavelengths above about 2000 nm, it is in particular the absorption by water in the skin tissue which becomes too large. Note that the short wavelength tail of this effect of coupling radiation into the skin may even be visible, since e.g. the human skin is perceived as somewhat translucent to red light.

Summarizing, the invention is based on the use of homogenized radiation that allows imaging that is less dependent on absorption by (hair) pigments, but more on color-independent physical effects on hair, like refraction. By providing a source that emits radiation which may easily be homogenized by the skin, and by increasing the relative amount of the homogenized radiation with respect to radiation that reaches the sensor in another way, the contrast of the image may be improved.

As some background information, a diffuse penetration depth D may be defined as:

$$D^{-1} = \sqrt{3A \times (A + (1-g) \cdot s)}$$

wherein
A is the absorption coefficient,
g is the anisotropy, and
s is the scattering coefficient.

The diffusion depth is an indication of the distance over which radiation may penetrate the skin tissue. A distance of at least about 1 mm, and preferably at least 5 mm, gives useful results as to homogeneity due to scattering in the skin, while the absorption is still low enough to allow sufficient re-emission of radiation by the skin, at least for the indicated wavelength region.

The reduced scattering $(1-g) \cdot s$ as a function of wavelength for two scattering mechanisms (Mie and Rayleigh) as well as the total of the scattering are slowly decreasing functions in the wavelength region of interest, with values between 10 and 20 $cm^{-1}$.

The absorption coefficient as a function of wavelength decreases rather sharply when going from the short wavelength end of the visible region to the long wavelength end, both for the skin tissue, and the melanosome (representative of melanin), blood and the epidermis. A minimum is encountered between about 800 and 1100, and a second, local minimum between about 1500 and 1850 nm. Combining the effects of scattering and absorption, it may be seen that radiation with a wavelength between about 700 nm and 1100 nm, and most preferably around 800 nm, may be used in the device of the present invention, since at these values the absorption is very low.

A remark to be made here is that the working of the device relates to a skin, since without a skin, no image will be formed. Whenever the features of the device according to the present invention relate to an image, to radiation for forming that image etc., the device should be in an operative position. For example, the radiation selection means increase the ratio of the intensity of radiation within said wavelength range that is receiveable by said imaging sensor after having traveled through said skin below the epidermis layer thereof, to the intensity of radiation within said wavelength range that is receiveable by said imaging sensor without having traveled through said skin below said epidermis layer, when the device is in an operative position with respect to the part of the skin to be illuminated.

Advantageously, the radiation detection means are capable of increasing the ratio of the intensity of radiation within said wavelength range that is receiveable by said imaging sensor after having traveled over at least 1 mm, and preferably at least 5 mm, through said skin below the epidermis layer thereof, to the intensity of radiation within said wavelength range that is receiveable by said imaging sensor without having traveled through said skin below said epidermis layer. At such a traveled length within the skin, an advantageous differentiation occurs between on the one hand radiation that is scattered in the skin but hardly absorbed by it, and thus provides the desired quasi-homogeneous illumination, and on the other hand undesirable radiation that is either absorbed in the skin and thus does not succeed in traveling that distance or does not enter the skin at all. Examples of the latter are radiation that irradiates the sensor directly, i.e. in a rectilinear optical path, specularly reflected radiation and radiation that is scattered by the skin surface or by hairs above the skin surface. The undesirable radiation may in itself be useful for other devices and methods, but for the present hair-detection device said undesirable radiation has no decisive effect on the contrast of the image.

Preferably, in an operative position of the device, the radiation selection means are able to reduce the intensity of the radiation within said wavelength range that is receiveable by said imaging sensor without having traveled through said skin below said epidermis layer to substantially zero. The number "zero" of the intensity should be viewed with respect to the intensity of the desirable radiation, i.e. of the quasi-homogeneous radiation. In order to prevent artifacts or any other unwanted influence on the image by said undesirable artifacts, the ratio between the desired radiation, i.e. the radiation that has traveled through the skin below the epidermis layer, or preferably over at least 1 mm, more preferably at least 5 mm, and the undesirable radiation as described above should be as high as possible, in particular going to the, only theoretically attainable, value of infinity. It is obvious that this value of the intensity and the ratio are to be determined when the device is in operation, since otherwise the intensity may simply be made zero by switching off the source or device, in which case the ratio could not be determined either.

Advantageously, said predetermined wavelength range is comprised in the range from 800 nm to 1100 nm or in the range from 1500 nm to 1850 nm. Radiation having a wavelength in these ranges is particularly useful in the device according to the invention, since these wavelengths show an advantageous ratio between absorption, which is low, and scattering, which is sufficiently strong to ensure a good homogeneity of the radiation that eventually escapes from the skin. The absorption by skin layers below the epidermis is sufficiently low for these wavelengths, mainly because absorption by haemoglobin drops rather sharply when leaving the visible region and entering the near-infrared wavelength region, and because melanin is practically absent below the epidermis. Furthermore, water, which is a main constituent of the skin, still has a low absorption at those wavelengths, the absorption showing a peak between about 1200 nm and 1500 nm and, after going through a local minimum between about 1500 nm and about 1850 nm, reaches values which quickly loose much of their practical interest.

Advantageously, said source comprises an incandescent lamp with a filter having a band edge between about 700 and about 1500 nm, or an infrared laser, or an infrared LED. Note that the filter may be a band pass filter or a high pass filter, as long as the filter is more transmissive in the wavelength range of interest. Although other radiation sources are not excluded, the above-mentioned sources offer the advantage that they may be selected to emit radiation which is to a large extent, or almost exclusively, in the desired wavelength range, thereby precluding that the skin to be treated heats up due to absorption of the remaining radiation outside the desired wavelength range.

In particular, many lasers and laser diodes and LEDs are available that emit (near) monochromatic radiation in the desired wavelength range. A large part of the desired wavelength range, in particular from about 750 nm to about 2000 nm, is in the near-infrared region of the spectrum. Hence a near-infrared laser/laser diode/LED is preferable. Additional advantages of these radiation sources are that they may be compact, powerful and intense sources, with furthermore a rather high efficiency and a long life.

Alternatively, an incandescent lamp may be used, more preferably a halogen incandescent lamp. This is a very simple and cheap source of radiation, that emits mostly in the desired wavelength range. By combining the incandescent lamp with an optional appropriate filter that absorbs radiation outside the desired wavelength range, possibly unpleasant or even painful absorption of excess radiation by the skin can be prevented. Preferably, such a filter is a high pass filter or band pass filter, having a band edge near or at the beginning of the short wave edge of the desired range, i.e. between around 700 and 1000 nm.

In a preferred embodiment, the imaging sensor comprises a CCD camera or a CMOS sensor. Such imaging sensors offer a versatile and mature technology, and are relatively cheap, sufficiently compact and sensitive for the purpose of imaging. Even for example standard optical CCDs, that are in use in optical cameras etc., may be used for the present device, as many such CCDs are sufficiently sensitive in at least a part of the desired wavelength range, say up to 1000 nm. Alternatively, and advantageously, CCDs etc. with improved near-infrared sensitivity may be used, preferably when the sensitivity to radiation outside the preferred wavelength range is decreased, in particular the sensitivity to visible optical radiation. This is advantageous in that it decreases the possibly undesirable influence of said radiation on the image formed by the imaging sensor.

In an advantageous embodiment of the device, the imaging sensor comprises a filter having a band edge between about 700 and 1500 nm. Again, the filter may be a high pass filter or a band pass filter that is more transmissive for wavelengths longer than the band edge. Such an imaging sensor is less sensitive to radiation in the undesired wavelength range that is still able to reach the sensor, e.g. scattered light or ambient light. Hence the attainable contrast is higher. The exact location of the band edge depends on the steepness of that edge.

For example. a very steep band edge may be centered around about 700 nm, while still offering a broad useful wavelength range, while a relatively flat band edge is preferably centered about a longer wavelength, since otherwise too much undesired radiation could pass the filter.

In a special embodiment of the device, the imaging sensor has a sensitivity as a function of wavelength which has a maximum in said predetermined wavelength range. Optimizing the sensor sensitivity is an alternative or additional way of improving the attainable contrast of the image. Various ways of optimizing or even maximizing this sensitivity in the desired wavelength range are known to the skilled person, such as appropriate selection of the radiation sensitive material. Again, a relatively reduced sensitivity to radiation outside the desired wavelength range ensures that the influence of such radiation is diminished.

Advantageously, the source is able to emit linearly polarized radiation or comprises a first radiation selection means comprising a first linear polarizer, and the imaging sensor comprises a second radiation selection means comprising a second linear polarizer. The first linear polarizer or the radiation emitted by the source that is able to emit linearly polarized radiation has a first direction of polarization, and the second linear polarizer preferably has a second direction of polarization, which is substantially perpendicular to the first direction. In this way, it is possible to prevent unwanted radiation from reaching the imaging sensor, or at least to improve the ratio between desired and undesired radiation. Radiation emitted by the source passes the first linear polarization, and obtains a first direction of polarization. If this polarized radiation is either rectilinearly transmitted to the imaging sensor, or is specularly reflected by the skin or some other object, the polarization does not change substantially, and will hence be stopped by the second linear polarizer in front of the imaging sensor. Contrarily, radiation that has been coupled into the skin, and is scattered a number of times, loses its polarization, and will be transmitted partly by the second polarizer. Note that other types of complementary polarizers may also be used.

In another embodiment, the radiation selection means comprise a circumferential wall around at least one of the imaging sensor and the source, the wall being substantially opaque for said predetermined wavelength range. This is an alternative or additional measure to improve the ratio between desired and undesired radiation, and thus the contrast of the image. Herein, a physical barrier is present between the source of radiation and the imaging sensor, in the optical path of the emitted radiation. This physical barrier will co-operate with the skin, when the device is in an operative position, to filly block the undesired radiation. In this way the desired radiation, that is coupled into the skin, may pass through the skin under the wall and reach the sensor, while the undesired radiation will be blocked by the opaque wall, whether it be reflected or direct radiation etc. Note that in principle it is not necessary to have a circumferential wall around the source or the imaging sensor, since any opaque wall there between would function as well. However, then there would be the possibility of stray light entering the sensor.

The circumferential wall need not have large dimensions. In fact it is the edge of said wall which co-operates with the skin in the operative position of the device to block radiation. Hence, it is also possible to provide only a radiation window in a housing around the source and/or the imaging sensor. This will be elucidated later herein below.

In a special embodiment of the hair-detection device according to the invention, the radiation selection means comprise a substantially opaque source housing around the source, the source housing having a source window for emitting radiation, the source window being sealingly placeable on the skin.

Alternatively or additionally, the radiation selection means comprise a substantially opaque sensor housing around the imaging sensor, the sensor housing having a sensor window for receiving radiation, the sensor window being sealingly placeable on the part of the skin to be illuminated.

Herein, the word "sealingly" should be interpreted in view of the optical radiation being blocked. Whether a gas-tight sealing or other type of sealing is obtained is completely irrelevant. Furthermore, the term "substantially" is to be interpreted as meaning "as much as possible", and at least 90%. Note that quantum mechanically it is possible in most cases that there is still a small transmission. For practical purposes, however, this is completely irrelevant, and it is easy to attain more than 99% blocking of undesired radiation.

It is advantageous to provide the hair-detection device with a diaphragm, preferably an adjustable diaphragm. This offers the possibility to block stray radiation from the environment, and to adjust the depth-of-field of the image, which may be useful for evaluating the image.

It may also be advantageous to provide the imaging sensor with an optical system having a focal length which is at least half as large as a diameter of the sensor window, preferably at least as large as the diameter of said sensor window. Generally speaking, by selecting a ratio between focal length and sensor window diameter which is high, one is able to block stray radiation that would otherwise diminish the contrast of the image. Again, selecting a larger focal length increases the depth-of-field.

In a preferred embodiment, the source and the image sensor are accommodated in a substantially opaque common housing with at least one window for transmitting radiation. Such a window is preferably sealingly placeable on the part of the skin to be illuminated or imaged. The presence of such a common housing is useful in preventing ambient radiation from disturbing the imaging. In fact, many of the above-mentioned measures of improving the ratio of the desired radiation to the undesired radiation have a much larger effect in combination with such a common housing. For example, in the presence of such an opaque common housing, providing two crossed polarizers, as in one of the preferred embodiments, suffices to block most of the undesired radiation, while in the absence of such a common housing the imaging could possibly suffer from ambient radiation. Note however that a possible solution in that case may be to perform the imaging in the dark. In that case, the wall of the room where the imaging is performed might be deemed the common housing. It is furthermore remarked here that the source and the imaging sensor may be separate or separable items, which offers advantages in maintenance and upgrading, but that they may also be integrated.

In a preferred embodiment, said common housing has a source window for emitting radiation and a separate sensor window for receiving radiation, wherein at least one of the source window and the sensor window are sealingly placeable on the skin. This embodiment offers the advantage that the radiation may be coupled into the skin via a first window, the source window, while the radiation for the imaging sensor may be coupled out of the skin via a second window, the sensor window, which is located at a certain distance from the first window. This favors selection of radiation that has actually traveled through the skin, as other radiation will at least partly be blocked by the housing and or the skin surface. Note that this is especially the case when both the source window and the sensor window are sealingly placeable on the skin, e.g. when both are present in one side of a common housing. However, even in the case where only one of the source window and the sensor window is sealingly placeable on the skin, the contrast may be improved.

It is remarked here that it is not necessary to provide separate windows for the sensor and the source, but that one window may suffice. As an example, when the source emits polarized radiation, and the imaging sensor is sensitive only to cross-polarized radiation, e.g. due to the presence of appropriate polarizers, it may suffice when the radiation is coupled into the skin part under the window, is scattered within the tissue of that skin part, and is re-emitted there from, since specularly reflected other radiation is effectively blocked.

In the context of the present invention, a window is an opening in a wall or the like, which opening may optionally be covered with a cover plate which is transparent to the radiation.

Advantageously, the distance between said source window and said sensor window is at least 0.1 mm, more preferably at least 1 mm, and even more preferably at least 5 mm. Such distances ensure not only that the radiation will be sufficiently homogenized through multiple scattering in the skin tissue, but also that the possibly present undesired radiation has been absorbed by the skin or by an intermediate opaque wall, housing or other radiation blocking part of the device.

A special embodiment of the hair-detection device according to the invention comprises a plurality of said sources arranged around said sensor window. Providing such a plurality of sources offers a more homogeneous intensity distribution for the sensor window. Since the intensity will drop as a function of the distance to the source or source window, providing a single source will give an uneven intensity distribution. This may of course be corrected for by employing suitable correction programs in an optionally provided imaging processing unit etc. Furthermore, depending on the average scattering length in the skin of the radiation used, and on the dimensions of the windows, this drop in intensity may be sufficiently small. However, multiple sources offer better homogeneity and more design flexibility. Preferably sources are located opposite each other with respect to the sensor window, and preferably in a regular fashion. Alternatively, a single source may be used, with a plurality of exit locations in the form of a plurality of source windows. Furthermore, optical fibers or the like may be used to couple the radiation into the skin. In a sense, the optical fibers may be deemed very elongate cover plates for a source housing.

It is remarked here that such a plurality of sources as described for the above embodiment is also possible for all other embodiments, even when the embodiment relates to "a source" or "the source". The same holds, among others, for the source window(s) and housings.

The hair-detection device according to the present invention offers an image with improved contrast for many situations, such as hairs and skin of about the same visible color, e.g. white hairs on a white skin. This improved contrast may be used when assessing the skin with the human eye. Any desired measure may thereupon be taken, such as removal of the hair by mechanical means etc. Preferably, the hair-detection device further comprises an image processing unit for determining the position and/or orientation of a hair from said image. This offers data or a signal that relates to the position and/or orientation of a hair on the skin. These data or this signal may be used by the device or any other apparatus for carrying out any desired after-treatment, be it as simple as counting the hairs, or e.g. shaving or depilating the skin.

The invention further relates to a hair-removing device comprising a hair-detection device according to the invention. The hair-removing device may be operated on the basis of visual information obtained by an operating person. Preferably, however, the hair-removing device is coupled to an image processing unit, such that the hair-removing device is operated by the image processing unit or a control unit that is fed by input from the image processing unit. This is particularly useful when the hair-removing device comprises an adjustable laser beam source that is controllable by said image processing device, e.g. a laser source and a laser beam manipulator that is controllable by the control unit coupled to the image processing device.

A useful operating method would then be to determine a hair position with the hair-detection device according to the invention, adjust a laser beam by means of the laser beam manipulator, such that it is directed to the hair or root thereof, and provide sufficient laser energy to burn the hair or root thereof, such that the hair may be removed.

BRIEF DESCRIPTION OF THE DRAWINGS

Embodiments of a hair-detecting device and of a hair-removing device in accordance with the invention will now be described in detail with reference to the accompanying Figures, in which.

DETAILED DESCRIPTION OF THE INVENTION

Figure 1:
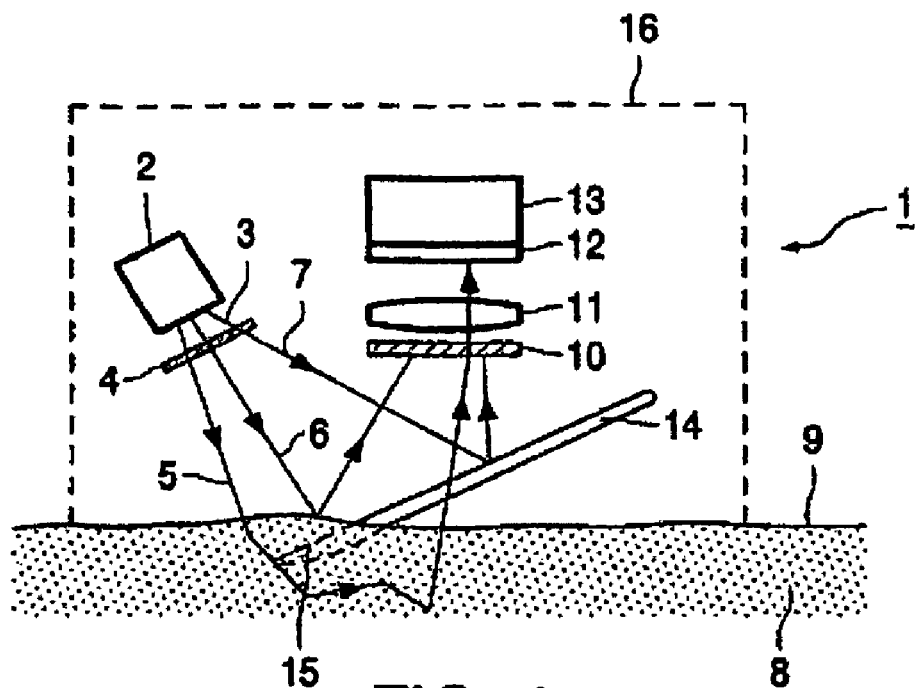
FIG. 1 diagrammatically shows a first embodiment of a hair-detecting device according to the invention.

FIG. 1 diagrammatically shows a first embodiment of a hair-detecting device 1 according to the invention. Herein, 2 is a source of radiation, emitting a beam 3 of radiation. A first polarizer is denoted by 4. Three rays 5, 6, 7 are shown to pass the polarizer 4. Reference numeral 8 denotes a skin having a surface 9. A second polarizer is denoted by 10. Reference numeral 11 denotes an optical system, 12 a CCD imaging sensor and 13 denotes a control unit. Reference numeral 14 denotes a hair, having a subcutaneous part 15. An optional box or housing is denoted by 16.

In the hair-detecting device 1, a source 2 emits a bundle 3 of radiation. The radiation 3 preferably comprises radiation in a wavelength range from 700 nm to about 2000 nm, more preferably between about 700 nm and 1100 nm, most preferably about 800 nm.

A first polarizer 4 is positioned in the beam 3. Radiation from beam 3 will have a direction of polarization after having passed the first polarizer 4. A first ray 5 enters the skin 8 through surface 9, and is scattered a number of times in the skin before it leaves the skin 8 through surface 9 and travels towards the second polarizer 10. The second polarizer 10 has a polarizing direction which is perpendicular to the polarizing direction of the first polarizer 4. Hence, radiation that has passed the first polarizer 4 and is specularly reflected will be blocked by second polarizer 10. This is shown by the second ray 6, which is specularly reflected off the surface 9, and the third ray 7 which is reflected by the hair 14. Both rays 6 and 7 are blocked by the second polarizer 10, while the first ray 5 passes the second polarizer 10, because after multiple scattering inside the skin 9, its direction of polarization has been lost. After having passed the second polarizer 10, the first ray 5 will go through an optical system 11, here denoted as a simple lens. Note that the optical system 11 may comprise several lens elements. Finally, first ray 5 will be detected in a CCD imaging sensor 12, which is coupled to a control unit 13. Control unit 13 processes the image that is detected by the CCD imaging sensor 12. The control unit 13 may further comprise, or be coupled to, e.g. a computer, a screen or a further processing device (not shown).

Note that in the above embodiment the first polarizer 4 may be dispensed with, if the source 2 of radiation emits polarized radiation, as does a laser diode.

The first ray 5, and a number of comparable rays that have traveled through the skin, provide substantially homogeneous lighting, which will form an image of a hair 14, as well as of a part of the subcutaneous part 15 of the hair on the CCD imaging sensor 12, as has been explained above.

The box 16 is shown in a dashed line to indicate that it is optional. In principal, the hair-detecting device 1 may be used under circumstances in which there is no or only a low disturbing light intensity. This may be achieved by using the device 1 as a whole in the dark or in ambient light to which the CCD is not sensitive. The latter may be achieved by suitable filtering or by selecting suitable lighting, e.g. sodium vapor or other monochromatic lighting. Another possibility is to use the box 16 around the hair-detecting device 1 in order to substantially or completely shield the device 1 from ambient light. Such a box 16 may be a separate part. Alternatively, the hair-detecting device 1 may be built into the box 16. In operation, the box will be placed on a body part with its open side facing the skin. The box may have any suitable shape, e.g. square, cylindrical etc.

Figure 2:
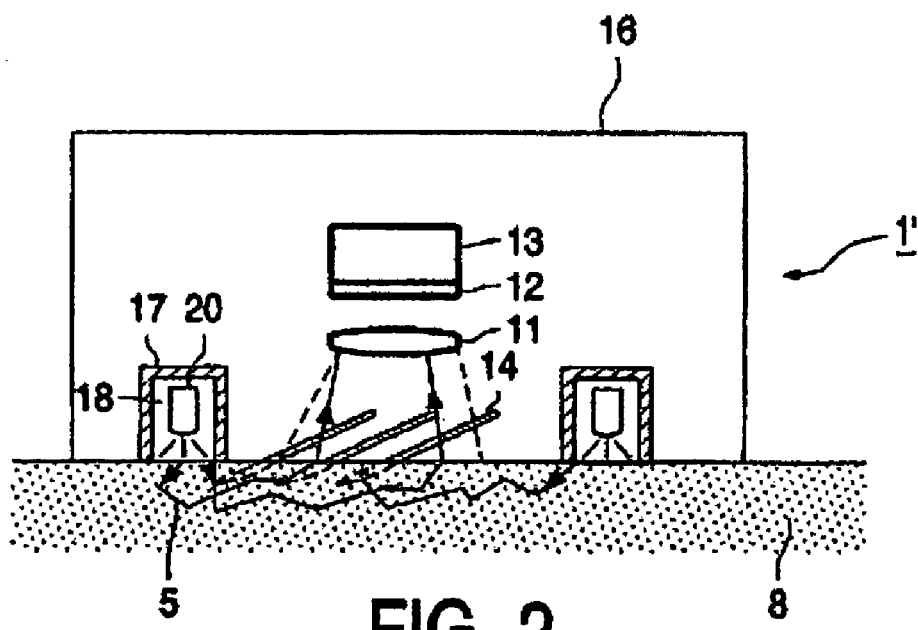
FIG. 2 is a diagrammatic cross-section of a second embodiment of a hair-detecting device according to the invention.

FIG. 2 diagrammatically shows a second embodiment of a hair-detecting device 1' according to the invention. Herein, similar parts are denoted by the same reference numerals.

This device 1' comprises a box 16 provided with 2 recesses 18 with a wall 17. In the recess 18, a source 20 of radiation is accommodated. The source 20 emits rays 5 of radiation, which in operation enter the skin 8 and are scattered therein. After leaving the skin 8, the rays 5 travel through an imaging optics 11 towards an imaging sensor 12, which is coupled to a control unit 13. All parts mentioned are accommodated in a housing 16 having an open side which in operation of the hair-detecting device faces towards the skin 8.

An advantage of this embodiment is that only radiation which actually enters the skin, i.e. passes the epidermis, will be used in the imaging process. Hence, in principal, any light source may be used that emits in the useful range of radiation. Of course, it will be preferred to have a relatively high emission in the preferred wavelength region, and a relatively low emission in other wavelength regions which are more easily absorbed in the skin. This will not only ensure a high efficiency of the hair-detecting device, but it will also help reduce any sensations of heat or pain in the skin. Useful sources 20 of radiation are infrared LEDs and infrared laser diodes.

The recesses 18 may be provided as chambers having a wall 17 in an otherwise hollow space within the box 16, or e.g. as a recess in an otherwise solid part of the device 1'. Note that the relevant criterion is that substantially no radiation emitted by the source 20 reaches the imaging sensor 12 directly, i.e. rectilinearly, or via scattering by the surface of the skin 8.

The housing 16 may have an open side that, in operation, faces the skin 8. Alternatively, the housing may comprise one or more windows (not indicated). At least one window will transmit incident radiation towards the imaging sensor 12, while at least one optional window will transmit radiation emitted by source 20. By providing such windows, a completely sealed construction may be obtained. This offers protection against the ingress of dust, water etc.

The imaging sensor 12 may be any appropriate, known imaging sensor. Examples include a CCD matrix sensor or a CMOS optical sensor, etc. The imaging sensor 12 should of course be sensitive to the radiation used. Since in many cases near-infrared radiation is used, sensitivity in this wavelength range should be sufficient or preferably optimized. Standard CCD-sensors are sufficiently sensitive for adequate image capturing. However, CCD elements are available which have been optimized to provide an increased sensitivity in the infrared region. The same holds for various other types of optical sensors. If, at the same time, the sensitivity to other radiation, which is not used in the imaging process, is decreased, an even more improved contrast is achievable. An example of such other radiation is visible light, especially of comparatively short wavelengths.

The control unit 13 may again comprise any device for collecting and evaluating the signals from the imaging sensor 12, in order to obtain an image and/or to drive or control any other apparatus. In many cases, the control unit may comprise electronic circuitry, such as a programmed or programmable chip or computer.

Figure 3:
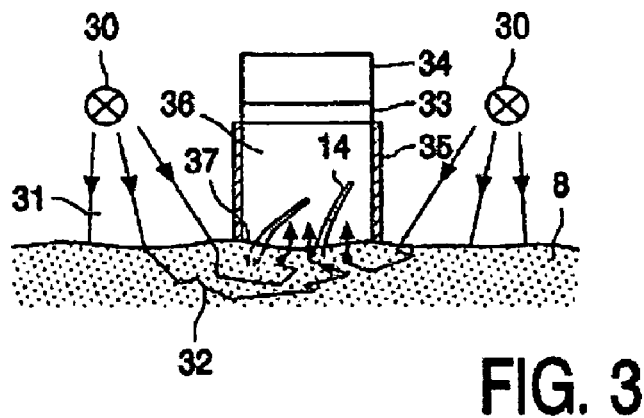
FIG. 3 is a diagrammatic cross-section of a third embodiment of a hair-detecting device according to the invention.

FIG. 3 diagrammatically shows a third embodiment of a hair-detecting device according to the invention. Herein, 30 denotes a source of radiation 31. Rays 32 of said radiation 31 enter the skin 8 and are scattered therein. Re-emitted radiation will travel towards imaging sensor 33, which may be connected to a control unit 34.

Said radiation is contained within the chamber 36 which is surrounded by an opaque wall 35 and has an opening 37. On the skin 8, hairs 14 are present.

A feature of this embodiment of the hair-detecting device according to the invention is that only radiation which has traveled through the skin 8 may reach the imaging sensor 33. Hence it is not necessary to contain the radiation 31 emitted by the sources 30. In fact, any ambient light which would add to the useful radiation may be advantageous in the present embodiment. Omitting any type of housing for the sources 30 may be advantageous in respect of improved cooling possibilities.

The source 30 may again be any type of radiation source that emits at least partially in the desired wavelength region. Apart from the already mentioned infrared LEDs and infrared laser diodes, other sources such as (halogen) incandescent lamps are not excluded.

Similarly, the imaging sensor 33 may be of any known type. Note that in this case a separate optical system has not been indicated. It may e.g. be that the imaging sensor 33 itself comprises such optical parts. It may for example be possible to use microlenses in front of the radiation-sensitive parts of the imaging sensor 33. In other cases, an appropriate optical system may be added to the imaging sensor 33.

The opening 37, through which radiation may reach the imaging sensor 33, may be covered by a cover plate through which the radiation may pass. Such a cover plate may be useful, not only to protect the imaging sensor 33 against dust, damage etc., but also to obtain a well-defined image plane, which is also kept at a constant distance. The presence of a cover plate may also help to press the hairs 14 against the surface of the skin 8. In that case, a much shallower depth-of-field is allowable, without the quality of the image of the skin being adversely affected. This is particularly useful when using diffuse lighting.

Figure 4A:
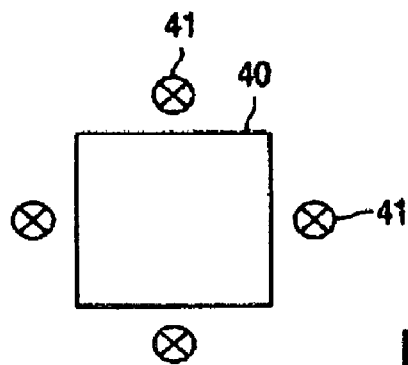
FIGS. 4a, 4b and 4c diagrammatically show a bottom view of three alternative embodiments of a hair-detecting device according to the invention.
Figure 4B:
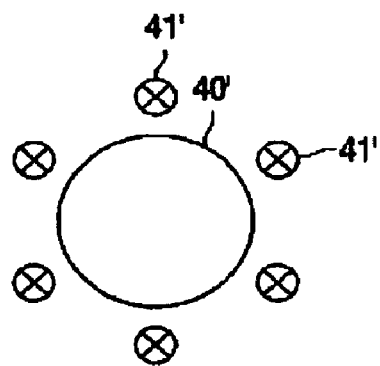
Figure 4C:
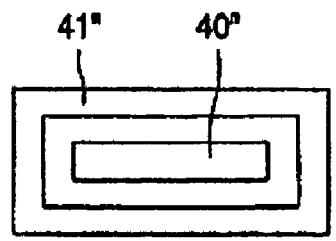

FIGS. 4a, 4b and 4c diagrammatically show a bottom view of three alternative embodiments of a hair-detecting device according to the invention. In FIG. 4a, 40 denotes an imaging sensor. Alternatively, 40 may denote a chamber that will contain the radiation traveling towards an imaging sensor, or alternatively a window for passing radiation towards the imaging sensor. In this case, 4 radiation sources 41 are shown, although it goes without saying that this number may be any desired number from one and up.

It is advantageous to locate the radiation sources 41 close to the imaging sensor 40. This will ensure that the radiation travels a relatively short distance within the skin. Absorption may thus be minimized, and generally, a relatively high intensity of re-emitted and thus useful radiation is achieved.

In FIG. 4b there is shown a substantially circular optical sensor 40' surrounded by, in this case, 6 radiation sources 41'. By providing a circular sensor (or window etc.), surrounded by a larger number of radiation sources 41', a more homogeneous intensity distribution for the radiation used in the imaging process may be obtained. Using a larger number of radiation sources 41 has the additional advantage that the local intensity of radiation which is coupled into the skin may be lower than when using fewer radiation sources 41', such as only one radiation source. This not only reduces possible pain or other feelings of discomfort for the subject being treated, but also allows the use of low-power radiation sources.

Note that, in principal, the shape of the imaging sensor 40', or of the cover plate etc., may be selected as desired, each shape having possible advantages. For example, a circular shape as shown in FIG. 4b provides generally a more homogeneous intensity distribution. The square shape as shown in FIG. 4a offers the advantage that it is relatively easy to cover a part of the skin having a surface area which is larger than the surface area of the imaging sensor 40. Such a part of the skin can be treated or imaged by locating the imaging sensor 40, or the cover plate etc., in contiguous locations on the part of the skin. This is possible without overlap, which is not the case for e.g. a circular or oval shape.

FIG. 4c diagrammatically shows a bottom view of the third embodiment of a hair-detecting device according to the invention. Herein, 40" is an imaging sensor, surrounded by a light source 41".

Note that in this case the light source is a spatially continuous light source, instead of a number of discrete light sources. This offers even better homogeneity of the intensity distribution. Such a continuous light source 41" may be obtained by e.g. phosphorescent or fluorescent lighting, gas discharge lighting etc. An alternative may be to provide for quasi-continuous lighting by using either a large number of very small light sources, or fiber optics to distribute the radiation from one or more discrete light sources etc.

It is advantageous to provide a stroboscopic source of radiation for imaging, which emits in pulses, instead of temporally continuously. This offers the advantage that an image may be determined without smearing effects. In other words the definition of the image may be increased. This is useful e.g. in the case of a shaving device, because such a device is normally moved over the surface of the skin, while still images of individual hairs are to be determined.

Figure 5:
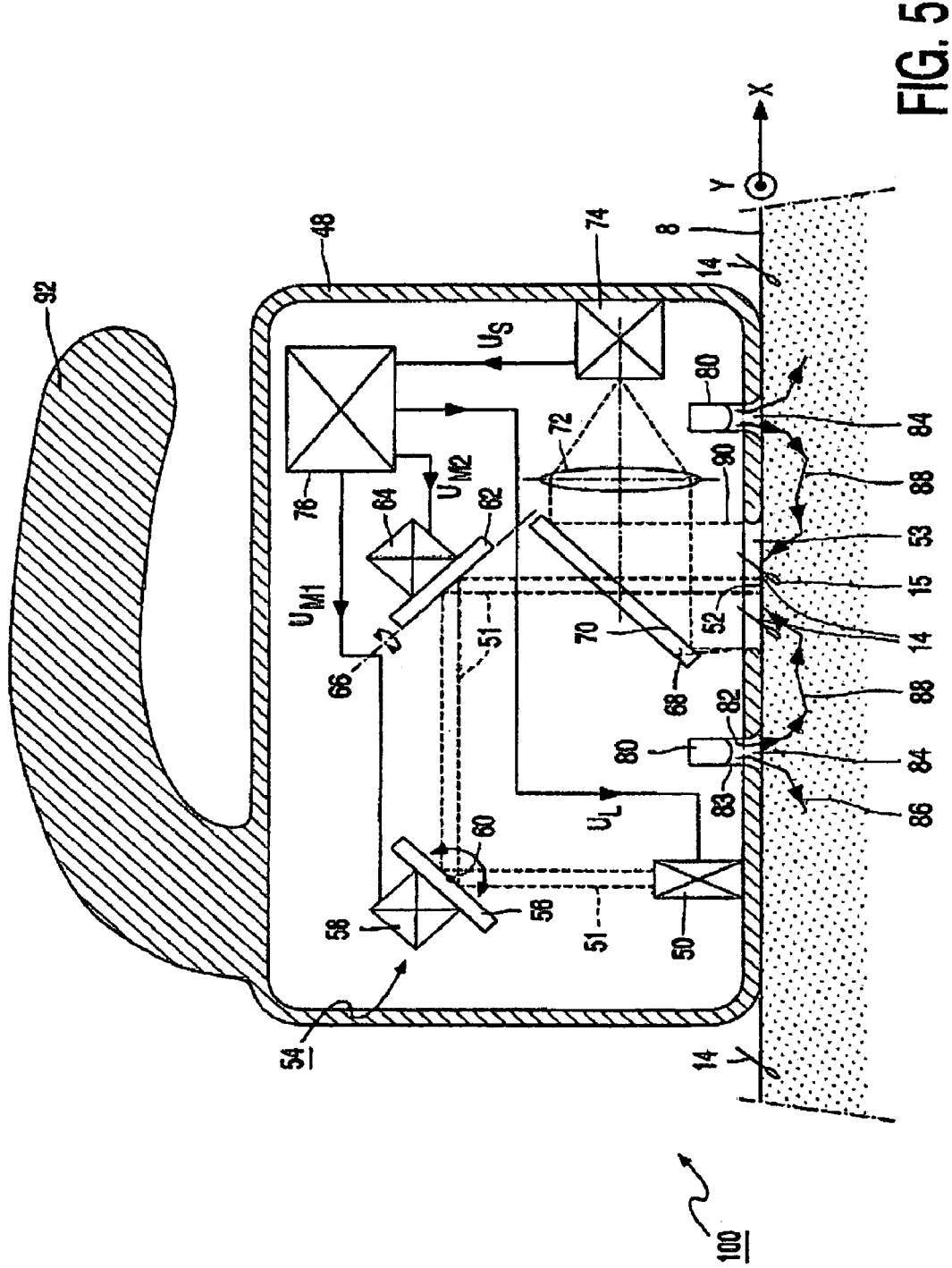
FIG. 5 diagrammatically shows a cross-section of a hair-removing device according the invention.

FIG. 5 diagrammatically shows a cross-section of a hair-removing device according to the invention.

In the device 100, 48 is a housing. 50 denotes a laser source, emitting a laser beam 51. Reference numeral 54 denotes an adjustable laser beam manipulator, comprising a first mirror 56 which, by means of a first actuator 58, is rotatable around a first axis 60. It further comprises a second mirror 62, which, by means of a second actuator 64, is rotatable around a second axis 66. The adjustable laser beam manipulator 54 reflects the laser beam 51 towards a target position or spot 52 in a first window 53 in the housing 48 on skin 8.

Reference numeral 68 is a selective mirror having a mirror surface 70. Reference numeral 72 is a lens and 74 is an imaging sensor.

Reference numeral 76 is a control unit, which is connected to a first and second actuator 58, 64, and to the laser source 50 and the imaging sensor 74. Reference numeral 80 denotes a radiation source in a chamber 82 having a wall 83 and emitting radiation through a second window 84. The emitted radiation comprises a first ray 86 which is lost in the skin 8, as well as a second ray 88 which is able to reach and pass first window 53. All such rays 88 will generally form a beam 90 for imaging hairs 14 and possibly hair roots 15.

The hair-removing device 100 according to the invention comprises a hair-detecting device according to the invention. The hair-detecting device may be considered to comprise a source of radiation 80, the appropriate windows 84 and 53, an optics system 68, 70, 72, an imaging sensor 74 and a control unit 76. Generally, any hair-detecting device according to the invention may be used alternatively. The hair-detecting device as described in the present embodiment will be elucidated further below.

The hair-removing device 100 may e.g. be an epilation device, a shaver etc. By means of the device 100, hairs 14 present on the skin 8 can be removed. If a hair 14 is to be removed, the spot 52 of the laser beam 51 must be approximately in a position on the skin 8 where the hair 14 crosses the surface of the skin 8, or in a position below which a root 15 of the hair 14 is present. The laser beam 51 contains monochromatic light with a wavelength which is well-absorbed by the hair 14 and preferably substantially not absorbed by tissue of the skin 8. The result is that predominantly the root 15 of the hair 14 is strongly heated by the laser beam 51, such that either the root 15 is damaged and/or dies, or the hair 14 is cut through or otherwise affected, and may be removed mechanically. A good optical selectivity between the hairs 14 and the tissue of the skin 8 is achieved with a wavelength between approximately 650 nm and 1200 nm in the case of a white skin with dark hairs. Light of such a wavelength is well-absorbed by melanin, a pigment which occurs in a high concentration in dark hairs and only in a low concentration in a white skin. Note that melanin is believed to be present in sufficient quantities even in lighter hairs. Light with such a wavelength is also only moderately absorbed by water, by haemoglobin, a red pigment in blood, and by keratin. In the case of a light shaver, i.e. a device which is used to burn through the hairs, it may be an option to select a wavelength which is shorter than 650 nm, because in principal the light need not penetrate into the skin. An advantage will be that there is a better selectivity between the light for actual hair removal and the light or radiation used for imaging.

Furthermore, a sufficient pulse duration and energy density of the laser beam 51 are required for effective operation of the hair-removing device 100. The person skilled in the art will have no problem selecting the required values for the relevant parameters, such as disclosed in WO 00/62700. This will not be discussed in any further detail here. Note, however, that in the case that a hair shaver is used, the required energy density is much lower. This has the advantage that there is less risk of damage to other parts of the skin.

Another important remark is that, although a laser source 50 is shown as the operative radiation source, this may also be another kind of appropriate source, such as any source that emits radiation of sufficiently high energy and sufficiently high concentration in the required wavelength region.

Examples are (halogen) incandescent lamps, (short arc) gas discharge lamps, LEDs etc. Moreover, it is not even necessary to use radiation as the operative agent for hair removal. Other known devices or techniques may also be employed, such as electric needle-epilation. A relevant criterion would be that the employed technique is operative locally, i.e. at the level of a single hair. After all, in this case it is of importance to be able to direct the operative agent (light, needle etc.) to a specific hair, in which case the hair-detecting device according to the invention will be useful. Herein below, the rest of the description will concentrate on laser epilation, although the above techniques are explicitly included as a possibility.

The laser beam 51 can be accurately positioned in the target position or spot 52 by means of the laser beam manipulator 54, while an image of a part of the skin 8 being treated may be obtained by means of a hair-detecting device according to the invention, as built into the device 100.

The adjustable laser beam manipulator 54 is shown to comprise two mirrors, 56 and 62. Both mirrors are positioned at an angle of approximately 45° with respect to the window 53 which is to be placed against the skin 8. The first mirror 56 is tiltable through limited angles about a first axis 21, extending in the plane of the first mirror 56 and parallel to the first window 53, by means of a first actuator 58. Said actuator may be of any suitable type, and is hence indicated only diagrammatically. The second mirror 62 is tiltable around an axis 66 which crosses the first axis 60 perpendicularly. The second actuator 64 for tilting the second mirror 62 is also depicted only diagrammatically. In combination, the first and second mirror 56, 62 are able to guide the laser beam 51 over a part of the skin 8 to be treated, for example corresponding to the first window 53. Note that the first window 53 may be covered by a cover plate which is transparent to the laser beam and to the radiation emitted by the radiation source 80. Similarly, second window 84 may be covered by cover plates which are transparent to the radiation emitted by the radiation source 80, i.e. at least that part of the radiation which is used in imaging.

In the embodiment shown, the distance between the light sources 80 and the first window 53 is relatively large. This has only been done for the sake of clarity. In practice, it is advantageous to minimize the distance between the light source 80 and the first window 53, in order to obtain an intensity that is as high as possible.

The first actuator 58 and the second actuator 64 are operatively connected to the control unit 76. The control unit 76 controls actuation of the first and second mirror 56, 62, for positioning the spot 52 in a desired location. Said location may be determined by means of a hair-detecting device according to the invention. This will now be elucidated.

Radiation sources 80 emit radiation, at least a part of which is coupled into the skin 8 and, after being scattered at least once, reaches the first window 53. Said radiation is able to leave the skin 8, and thereby forms a more or less homogeneous source of radiation. Said homogeneous source of radiation forms an image of a hair 14 because said radiation is refracted by the hairs, especially near edges thereof. Because part of the radiation is refracted away at those edges, these edges appear as shadows on the image. The radiation with this information travels as a beam 90 towards a third mirror 68 and is reflected by mirror surface 70. The reflected beam passes lens 72 and is projected onto imaging sensor 74. The imaging sensor 74, for example a CCD sensor, forms an image of the part of the skin at first window 53. Said image, or the information thereof, is fed to the control unit 76. Said control unit 76 may comprise means, such as a computer program, for evaluating the image as determined by the imaging sensor 74. Any known means for recognizing hairs in the image, such as a LabView application or similar devices or programs, may be used to detect hairs in the image. Note that both visible ends of a hair may be discerned, since the "end" that enters the skin shows a gradually blurring contrast, while the other end shows an abrupt and sharp contrast. This is due to the fact that the skin is sufficiently transparent to the radiation, such that only scattering blurs the image, which increases with depth.

The laser beam 51 is seen to pass through the third mirror 68, while the beam 90 of radiation that has passed through the skin 8 is reflected by the mirror surface 70. This difference need not be absolute, in that a part of the laser beam 51 may also be reflected by the third mirror 68, while a part of the beam 90 may be transmitted by the mirror 68. This may for example be achieved by embodying mirror 68 as a band-pass mirror which transmits in the narrow wavelength region of the laser beam 51 and reflects at least a part of beam 90. Otherwise, a generally semi-transparent mirror would suffice as well. Furthermore, it is possible to select a laser wavelength for the laser beam 51 which is outside the wavelength range of the radiation transmitted through the skin, or near a band edge thereof. For example, radiation transmitted through the skin has a wavelength of between 800 and 1200 nm, whereas a laser beam having a wavelength around 700 nm may be employed. It would then suffice if the third mirror 68 has a band edge between 700 and 800 nm. Alternatively, third mirror 68 may be moveable, such that it is removed out of the path of the laser beam at the moment when the laser source 50 is activated. Another alternative would be to use a switchable mirror which would normally reflect both the laser beam and the radiation in beam 90, but which mirror would be deactivated at the moment when the laser source 50 is activated. Yet another alternative would be to use a polarizing beam splitter, e.g. arranged such that the laser beam passes the beam splitter, while the radiation of beam 90 is (at least partly) reflected.

Useful radiation sources 80 for emitting desirable radiation in the wavelength region of 700 nm and longer wavelengths, in particular between 800 nm and 1200 nm and between about 1500 and 1850 nm, are infrared LEDs and/or infrared lasers or laser diodes.

The laser source 50 is also connected to and controllable by the control unit 76. The control unit 76 may e.g. control the laser source 50 such that the latter is activated only when a hair has been detected and the adjustable laser beam manipulator 54 has been set such that the spot 52 is in the correct position for removing the detected hair. In this way the radiation load on the skin is minimized.

An alternative embodiment of the adjustable laser beam manipulator 54 may be a single mirror which is pivotable around two mutually perpendicular axes. Alternatively, the laser beam 51 may be transmitted through a tiltable transparent plate or block. When incident at a non-right angle, the beam is displaced in a parallel direction, and this displacement may be influenced by tilting the plate. Many other alternatives will occur to the skilled person and will not be elucidated further.

The hair-removing device 100 will, when in use, be positioned on a part of the skin to be treated, for example to be depilated. To this end, the housing 48 is positioned on skin such that the first window 53 overlies the part of the skin to be treated. Handling of the device 100 may be facilitated by means of grip 92.

It is finally noted that the invention relates to a hair-detecting device, as well as a hair-removing device using said hair-detecting device, in which radiation that has been coupled into the skin is used as a means for improving contrast to detect hairs. The invention is characterized by the use of radiation that has traveled a certain distance through tissue of the skin below the epidermis, which stands in contrast to known methods that make use of radiation which is reflected at a surface, such as a skin or hair.

The invention claimed is:

1. A hair-detection device, comprising:
    a source of electromagnetic radiation having a first component that passes through skin and a second component that does not pass through the skin;
    an imaging sensor for having a first component that passes through skin and a second component that does not pass through the skin determining an image of a part of a skin to be illuminated by said electromagnetic radiation, the imaging sensor is sensitive to at least a predetermined wavelength range of said electromagnetic radiation selected from 700 nm to 2000 nm; and
    a radiation selection means for increasing a ratio of intensity of the first component of the electromagnetic radiation within said predetermined wavelength range to the intensity of the second component of the electromagnetic radiation within said predetermined wavelength range.

2. The hair-detection device according to claim 1, wherein the first component that passes through said skin over at least 1 mm.

3. The hair-detection device according to claim 1, wherein in an operative position of the device, the radiation selection means reduces the intensity of the second component of the electromagnetic radiation to substantially zero.

4. The hair-detection device according to claim 1, wherein said predetermined wavelength range is in the range from 800 nm to 1100 nm or in the range from 1500 nm to 1850 nm.

5. The hair-detection device according to claim 1, wherein said source comprises an incandescent lamp with a filter with a band edge between 700 and 1500 nm, an infrared laser, or an infrared LED.

6. The hair-detection device according to claim 1, wherein the imaging sensor comprises a CCD camera or a CMOS sensor.

7. The hair-detection device according to claim 1, wherein the imaging sensor comprises a filter having a band edge between 700 and 1500 nm.

8. The hair-detection device according to claim 1, wherein the imaging sensor has a sensitivity as a function of wavelength which has a maximum in said predetermined wavelength range.

9. The hair-detection device according to claim 1, wherein the source is able to emit linearly polarized radiation or comprises a first radiation selection means comprising a first linear polarizer, and wherein the imaging sensor comprises a second radiation selection means comprising a second linear polarizer.

10. The hair-detection device according to claim 1, wherein the radiation selection means comprise a circumferential wall around at least one of the imaging sensor and the source, the wall being substantially opaque for said predetermined wavelength range.

11. The hair-detection device according to claim 1, wherein the radiation selection means comprise a substantially opaque source housing around the source, the source housing having a source window for emitting radiation, the source window being sealingly placeable on the skin.

12. The hair-detection device according to claim 1, wherein the radiation selection means comprise a substantially opaque sensor housing around the imaging sensor, the sensor housing having a sensor window for receiving radiation, the sensor window being sealingly placeable on the part of the skin to be illuminated.

13. The hair-detection device according to claim 1, wherein the source and the imaging sensor are accommodated in a substantially opaque common housing with at least one window for transmitting radiation.

14. The hair-detection device according to claim 13, wherein said common housing has a source window for emitting the electromagnetic radiation and a separate sensor window for receiving radiation, wherein at least one of the source window and the sensor window are sealingly placeable on the skin.

15. The hair-detection device according to claim 14, wherein the distance between said source window and said sensor window is at least 0.1 mm.

16. The hair-detection device according to claim 13, wherein the device comprises a plurality of sources of electromagnetic radiation arranged around said sensor window.

17. The hair-detection device according to claim 1, wherein the device further comprises an image processing unit for determining at least one of a position and an orientation of a hair from said image.

18. A hair-removing device comprising:
    a source of electromagnetic radiation having a first component that passes through skin and a second component that does not pass through the skin;
    an imaging sensor for receiving the electromagnetic radiation and determining an image of a part of a skin to be illuminated by said electromagnetic radiation, the imaging sensor is sensitive to at least a predetermined wavelength range of said electromagnetic radiation selected from 700 nm to 2000 nm; and
    a radiation selection means for increasing a ratio of intensity of the first component of the electromagnetic radiation within said predetermined wavelength range to the intensity of the second component of the electromagnetic radiation within said predetermined wavelength range.

* * * * *